US009618503B2

(12) United States Patent
Benet Catalá et al.

(10) Patent No.: US 9,618,503 B2
(45) Date of Patent: Apr. 11, 2017

(54) METHOD FOR DETERMINING THE PRODUCTION OF REACTIVE OXYGEN SPECIES IN A CELLULAR POPULATION

(75) Inventors: Jordi Benet Catalá, Sant Cugat del Valles (ES); Agustín García Peiró, Barcelona (ES)

(73) Assignee: Universidad Autonoma De Barcelona, Bellaterra (ES)

( * ) Notice: Subject to any disclaimer, the term of this patent is extended or adjusted under 35 U.S.C. 154(b) by 0 days.

(21) Appl. No.: 13/883,562

(22) PCT Filed: Nov. 4, 2011

(86) PCT No.: PCT/ES2011/070756
§ 371 (c)(1),
(2), (4) Date: May 3, 2013

(87) PCT Pub. No.: WO2012/059615
PCT Pub. Date: May 10, 2012

(65) Prior Publication Data
US 2013/0224737 A1 Aug. 29, 2013

(30) Foreign Application Priority Data
Nov. 4, 2010 (ES) .................................. 201031624

(51) Int. Cl.
C12Q 1/68 (2006.01)
C12Q 1/24 (2006.01)
C12N 11/00 (2006.01)
G01N 33/50 (2006.01)

(52) U.S. Cl.
CPC ....... *G01N 33/5091* (2013.01); *G01N 33/502* (2013.01); *G01N 2500/10* (2013.01); *G01N 2800/367* (2013.01); *G01N 2800/7009* (2013.01)

(58) Field of Classification Search
CPC ............... G01N 33/50; G01N 2500/10; G01N 2800/7009; G01N 2800/367; C12Q 1/68; C12Q 1/24; C12N 11/00
USPC ............................................ 435/6.1, 30, 174
See application file for complete search history.

(56) References Cited

U.S. PATENT DOCUMENTS

| 4,176,953 A | 12/1979 | Bartoov et al. |
| 5,434,027 A | 7/1995 | Oshiba et al. |

FOREIGN PATENT DOCUMENTS

| GB | 2265709 | 10/1993 |
| WO | 9322053 A1 | 11/1993 |
| WO | WO 01/32802 | 5/2001 |
| WO | 2006/065900 | 6/2006 |
| WO | 2007085839 A1 | 8/2007 |
| WO | WO 2008/026205 | 3/2008 |
| WO | WO 2008/044138 | 4/2008 |
| WO | 2009/032040 | 3/2009 |
| WO | WO 2009/107769 | 9/2009 |

OTHER PUBLICATIONS

Ellsaesser et al. A New Method for the Cytochemical Staining of Cells Immobilized in Agarose; Histochemistry, vol. 80 (1984) pp. 559-562.*
Zini et al. Antioxidants and Sperm DNA Damage: A Clinical Perspective; Journal of Assisted Reproduction and Genetics, vol. 26 (2009) pp. 427-432.*
Fernandez et al. Simple Determination of Human Sperm DNA Fragmentation With an Improved Sperm Chromatin Dispersion Test; Fertility and Sterility, vol. 84, No. 4 (2005) pp. 59-66.*
Choi et al. A Quantitative Nitroblue Tetrazolium Assay for Determining Intracellular Superoxide Anion Productioin in Pahgocytic Cells; Journal of Immunoassay and Immunochemistry, vol. 27 (2006) pp. 31-44.*
Agarwal, et al., "Role of antioxidants in treatment of male infertility: an overview of the literature" Reproductive Biomedicine on-line; vol. 8, Issue 6 , pp. 616-627, 2004, abstract.
Aitken, et al., "Relative Impact of Oxidative Stress on the Functional Competence and Genomic Integrity of Human Spermatozoa"; Biology of Reproduction, vol. 59, pp. 1037-1046, (1998).
Aitken, et al., "On the possible origins of DNA damage in human spermatozoa", Molecular Human Reproduction, vol. 16, No. 1, pp. 3-13, 2010.
Angelopoulo, R. et al. "Spermatozoal sensitive biomarkers to defective protaminosis and fragmented DNA", Reproductive Biology and Endocrinology, 2007, 5:36 , 15 pp.
Athayde, et al., "Development o Normal Reference Values for Seminal Reactive Oxygen Species and Their Correlation With Leukocytes and Semen Parameters in a Fertile Population", Journal of Andrology, vol. 28, No. 4, 2007, pp. 613-620.
Carrell, et al. "Sperm DNA fragmentation is increased in couples with unexplained recurrent pregnancy loss", Systems Biology in Reproductive Medicine, 2003, vol. 49, No. 1: 49-55 (1pp), abstract.
Erenpreiss, et al., "Sperm chromatin structure and male fertility: biological and clinical aspects", Asian Journal of Andrology, 2006, vol. 8 pp. 11-29.
Esfandiari, et al., "Utility of the Nitroblue Tetrazolium Reduction Test for Assessment of Reactive Oxygen Species Production by Seminal Leukocytes and Spermatozoa", Journal of Andrology, 2003, vol. 24, No. 6, pp. 862-870.

(Continued)

*Primary Examiner* — Sharmila G. Landau
*Assistant Examiner* — Paul Martin
(74) *Attorney, Agent, or Firm* — Craig R. Miles; CR Miles P.C.

(57) ABSTRACT

The invention relates to a method for determining the production of reactive oxygen species in a cellular population. The invention also relates to a method for determining the need for an antioxidant treatment of a male subject, and to a method for identifying a substance that can reduce the reactive oxygen species in a cellular population.

13 Claims, 5 Drawing Sheets

(56) References Cited

OTHER PUBLICATIONS

Evenson, et al., "Data analysis of two in vivo fertility studies using Sperm Chromatin Structure Assay-derived DNA fragmentation index vs. pregnancy outcome", Fertility and Sterility, vol. 90, No. 4, 2008, pp. 1229-1231.

Evenson, et al., "Clinical aspects of sperm DNA fragmentation detection and male infertility", Theriogenology vol. 65, Issue 5, 2006, pp. 979-991.

Fernandez, et al., "Halosperm is an easy, available, and cost-effective alternative for determining sperm Dna fragmentation", Fertiity and Sterility, vol. 84, No. 4, 2005, pp. 860.

Greco, et al., "Reduction of the Incidence of Sperm DNA Fragmentation by Oral Antioxidant Treatment", Journal of Andrology, vol. 26, No. 3 2005, pp. 349-353.

Iwasaki, et al. "Formation of reactive oxygen species in spermatozoa of infertile patients", Fertility and Sterility, vol. 57 (2), 1992, 409-416 (Abstract 1 pp).

Lindgren, et al., "Cell-penetrating peptides", Trends in Pharmacological Sciences, vol. 21, Issue 3, 2000, pp. 99-103.

Lundgren, et al., "Cell Surface Adherence and Endocytosis of Protein Transduction Domains", Molecular Therapy (2003) 8, 143-150 (Abstract 1pp).

Ménézo, et al., "Antioxidants to reduce sperm DNA fragmentation: an unexpected adverse effect", Reproductive BioMedicine Online vol. 14, Issue 4, 418-421, 2007 (Abstract 1 pp).

Mostafa, et al., "Seminal reactive oxygen species-antioxidant relationship in fertile males with and without varicocele", Andrologia, vol. 41, Issue 2, Apr. 2009, pp. 125-129.

Naughton, et al., "Varicocele and male infertility: Part II: Pathophysiology of caricoceles in male infertility", Human Reproduction Update (2001) vol. 7 (5) pp. 473-481.

Ochsendorf,F.R., "Infections in the male genital tract and reactive oxygen species", Human Reproduction Update (1999) vol. 5 No. 5, pp. 399-420.

The Practice Committee of the American Society of Reproductive Medicine, Definition of "infertility", Fertility and Sterility, vol. 82, Suppl. 1 2004, 1 pp.

Sawyer, et al., Quantitative analysis of gene-specific DNA damage in human spermatozoa, Mutation Research vol. 529, Issues 1-2, 2003, pp. 21-34.

Schwarze, et al., "In vivo protein transduction: intracellular delivery of biologically active proteins, compounds and DNA." Trends in Pharmacological Sciences vol. 21.2 (2000) pp. 45-48.

Snyder, et al., "Cell penetrating peptides in drug delivery", Pharmaceutical Research, vol. 21, No. 3, 2004: 389-393 (Abstract 1pp).

Tesarik, et al., "Sperm nuclear DNA damage: update on the mechanism, diagnosis and treatment", Reproductive BioMedicine Online, vol. 12, Issue 6, 2006: 715-721 (Abstract 1 pp).

Tremellen, Kelton, "Oxidative stress and male infertility—a clinical perspective", Human Reproduction Update, vol. 14, No. 3, 2008, pp. 243-258.

Sikka, Suresh, C., "Oxidative Stress and Role of Antioxidants in Normal and Abnormal Sperm Function", Frontiers in Bioscience: a journal and virtual library 1, e78-86, Aug. 1, 1996, 17pp.

Twigg, et al. "Analysis of the impact of intracellular reactive oxygen species generation on the structural and functional integrity of human spermatozoa: lipid peroxidation, DNA fragmentation and effectiveness of antioxidants", Human Reproduction (1998) vol. 13, No. 6, pp. 1429-1436.

Zini, et al. "Reactive oxygen species in semen of infertile patients: levels of superoxide dismutase- and catalase-like activities in seminal plasma and spermatozoa" International Journal of Andrology, vol. 16, Issue 3, 1993, pp. 183-188, abstract.

Zini, et al. "Are Tests of Sperm DNA Damage Clinically Useful? Pros and Cons", Journal of Andrology, vol. 30, Issue 3, 2009, pp. 219-229.

Tunc, et al. Development of the NBT assay as a marker of sperm oxidative stress. Int'l Journal of Andrology, Oct. 2010, vol. 33(1), pp. 13-21 (abstract only).

Fernandez et al. The Sperm Chromatin Dispersion Test: A Simple Method for the Determination of sperm DNA Fragmentation. J of Andrology, Jan. 2003, vol. 24, No. 1, pp. 59-66.

Tunc, et al. Development of the NBT assay as a marker of sperm oxidative stress. Int'l Journal of Andrology, Feb. 2010, vol. 33(1), pp. 13-21 (abstract only).

Corresponding European Patent Application No. 11837612.8; EPO Office Communication dated Sep. 16, 2014, along with the Extended European Search Report, 8 pages total.

Corresponding European Patent Application No. 15199379.7; EPO Office Communication dated Mar. 4, 2016, along with the Extended European Search Report, 7 pages total.

Bettaieb et al. Thermotolerance induced at a fever temperature of 40 degrees C protects cells against hyperthermia-induced apoptosis mediated by death receptor signalling. Biochem Cell Biol., Dec. 2008, 86(6):521-38.

* cited by examiner

METHOD FOR DETERMINING THE PRODUCTION OF REACTIVE OXYGEN SPECIES IN A CELLULAR POPULATION

This application is the United States National Stage of International Patent Cooperation Treaty Patent Application No. PCT/ES2011/070756, filed Nov. 4, 2011, which claims the benefit of Spanish Patent Application No.: P201031624, filed Nov. 4, 2010, hereby incorporated by reference herein.

FIELD OF THE INVENTION

The present invention relates to a method for determining the production of reactive oxygen species in a cellular population. The invention also relates to a method for determining the need for antioxidant therapy for a male subject and to a method for identifying a substance that is able to decrease the reactive oxygen species present in a cellular population.

BACKGROUND OF THE INVENTION

Fertility is defined as the capacity of living beings to reproduce. Based on this concept, it is considered that sterility is the loss of this capacity and it is estimated that it affects 15% of couples of reproductive age. In approximately half of cases the male factor is present: in 20% it is exclusively male, in 38% it is predominantly female, and in another 27% it is considered mixed, whereas in the remaining 15% there is no specific cause, and in these cases it is classified as infertility of unknown origin or idiopathic. According to the American Society for Reproductive Medicine (The Practice Committee of The American Society for Reproductive Medicine, 2006), infertility is regarded as a pathology whenever a couple are unable to conceive in a minimum period of 12 months. Nevertheless, between 20% and 30% succeed in having children after this time.

For diagnosis of male infertility, in addition to the main parameters that are determined in semen analysis (sperm concentration, motility and morphology), recently a new parameter has begun to be considered: sperm DNA fragmentation. Analysis of sperm DNA fragmentation determines the existence of breaks in one or both DNA strands. This has attracted some attention because the presence of these breaks compromises an individual's capacity to have healthy children when the paternal genetic message is altered. In fact, in recent years several studies have demonstrated the presence of an increased percentage of sperm with fragmented DNA in infertile individuals relative to fertile individuals (Evenson D P et al. Theriogenology 15: 979-91 (2006)). The effect was immediate in the area of clinical diagnosis of male infertility and it has started to be evaluated as a marker of sperm quality since DNA fragmentation offers a value complementary to the parameters in semen analysis, although it is true that the predictive value with respect to fertility is still under investigation (Zini and Sigman. J Androl. 30(3): 219-29 (2009)).

At present, the values that associate DNA fragmentation with low potential for fertility "in vivo" or "in vitro" are stated to be in the range 30-40% of sperm affected (Evenson D P and Wixon R. Fertil Steril 90(4): 1229-31 (2008)). In these cases, the risk of recurrent abortions, implantation failure or abnormal embryonic development increases significantly (Carrell D T et al. Arch Androl 49 (1): 49-55 (2003)). Conversely, in fertile individuals without other disorders, the percentage of sperm with fragmented DNA is expected to be under 20%, whereas intermediate values between 20% and 30% of fragmentation might indicate an abnormal situation although it could still not be linked to infertility (Erenpreiss J et al. Asian J Androl 8(1): 11-29 (2006)).

The etiology of sperm DNA fragmentation is multifactorial and although the mechanisms that cause these alterations have partly been identified, the origin of this damage is not known with absolute certainty (Tesarik et al. Reprod Biomed Online 12: 715-21 (2006), Angelopoulo R et al. Reprod Biol Endocrinol 5: 36 (2007)). However, at an intrinsic level, it has been suggested that changes during spermiogenesis affect compaction of the sperm nucleus, producing a state of vulnerability to certain forms of oxidative stress that might cause breakage of DNA (Aitken R J and De Iuliis G N. Mol Hum Reprod. 2009 Jul. 31).

Oxidative stress is regarded as one of the main causes of sperm DNA fragmentation. Generally, oxidative stress means that a metabolic imbalance develops in the organ affected, so that the organism is incapable of quickly neutralizing the reactive oxygen species that are produced as a consequence of the constant supply of metabolic energy required for their activity. In this way, as they accumulate they produce damage in all the components of the cell, including the DNA, oxidation of polyunsaturated fatty acids and oxidation of amino acids in proteins.

Various studies have demonstrated that reactive oxygen species, both of endogenous and exogenous origin, can induce sperm DNA breakage in vitro or in vivo, confirming the part played by free radicals in the etiology of male infertility (Iwasaki A et al. Fertil Steril. 1992; 57: 409-16, Zini A Int J. Androl. 1993; 16: 183-8, Tremellen K Reprod Update. 2008 May-June; 14(3): 243-58).

It is estimated that between 25% and 50% of infertile patients have abnormal concentrations of reactive oxygen species (Twigg J et al., Hum Reprod. 1998; 13: 1429-36, Aitken R J et al., Biol Reprod. 1998; 59: 1037-46, Sawyer D E Mutat Res. 2003; 529: 21-34).

In the particular case of patients diagnosed with varicocele, the main disorder that can be corrected surgically, representing between 19% and 41% of cases of infertility, the presence of reactive oxygen species can be even greater compared to other infertile patients (T. Mostafa et al., Andrologia 41 (2009), pp. 125-129, Naughton C K. et al., Hum Reprod Update 7 (2001), pp. 473-481).

In this context, it seems obvious that rational treatment with antioxidant therapies could help to improve the integrity of sperm DNA, since its main effect is directed at maintaining homeostatic equilibrium by neutralizing reactive oxygen species. In fact, several studies have demonstrated a positive result of certain treatments with antioxidants on sperm DNA fragmentation and other important semen parameters such as sperm concentration, motility or morphology (Agarwal A. et al., Reprod Biomed Online. 2004 June; 8(6): 616-27, Greco E. et al., J. Androl. 2005 May-June; 26(3): 349-53, Ménézo Y J. et al., Reprod Biomed Online. 2007 April; 14(4): 418-21). Although there have been few such studies and the sample sizes are insufficient, the data currently available indicate that treatment with oral antioxidants contributes to preserving the integrity of sperm DNA. Ideally, administration of antioxidant treatments should be prescribed after determining the presence of oxidative stress in the patient's sample.

The determination of oxidative stress in semen samples in andrology laboratories is not included in routine practice because the existing methods are expensive, complex and lack standardization.

At present there are about 30 methods for determining oxidative stress (Ochsendorf FR. Hum Reprod Update. 1999 September-October; 5(5): 399-420). These methods are classified as direct methods, indirect methods and sentinel signs.

The direct methods determine the damage produced by the excess of reactive oxygen species against the phospholipids present in the plasma membrane or in DNA. The direct methods determine damage that is the end product of an imbalance between excessive production of free radicals and the cell's antioxidant capacity. This group may include the test for thiobarbituric acid, which requires high-performance liquid chromatography (HPLC) or determination of isoprostane 8-Iso-PGF2a or the c11-BODIPY test. These tests are quite promising but are not used routinely owing to their complexity.

The indirect methods are generally very sensitive and have the advantage that the normal values in fertile and infertile controls are relatively well defined. These methods determine the presence of reactive oxygen species (ROS hereinafter) in semen samples. The ROS include oxygen ions, free radicals and peroxides, both inorganic and organic. They are generally very small, highly reactive molecules that form naturally as a by-product of normal oxygen metabolism and have an important role in cell signaling. They are generally methods based on chemiluminescence using luminol or lucigenin (Athayde K S. et al. *J. Androl.* 2007, 28: 613-20). However, lucigenin tends to undergo autoxidation, affecting the results, and, furthermore, the analysis requires a luminometer, which is a very expensive instrument. Tunc et al. (Int. J. Androl, 33: 13-21) described an indirect fertility test based on detection of ROS using NBT as indicator. In cells that contain ROS, NBT is converted to formazan, producing a colored precipitate. However, this method has the disadvantage that the sperm in the sample tend to aggregate and sediment in the conditions in which they are incubated to lead to the formation of formazan, which makes it difficult to determine the percentage of sperm that contain ROS.

Finally, there is a set of indicators (sentinel signs) that indicate the presence of oxidative stress, namely: low sperm motility, teratozoospermia, presence of leukocytes in semen, increase in viscosity, HOST test positive or poor membrane integrity.

There is therefore a need to find a method that is economical and easy to carry out, for determining the presence of ROS in a cellular population.

SUMMARY OF THE INVENTION

In a first aspect, the invention relates to a method for determining the presence of cells that contain reactive oxygen species in a cellular population that comprises:
 a) contacting, in isotonic conditions, said cellular population with a thickening agent so that the motility of the cells of the cellular population is substantially reduced and with a compound that is an indicator of the presence of reactive oxygen species,
 b) maintaining the mixture obtained in step a) for a sufficient time for conversion of the indicator compound to a compound that is detectable in those cells that contain reactive oxygen species,
 c) putting the mixture obtained in b) with a gelling agent on a solid support in conditions suitable for gelling of the gelling agent to take place and
 d) identifying those cells in which the detectable compound appears where the presence of the detectable compound in a cell is indicative of the presence of reactive oxygen species in said cell.

In a further aspect, the invention relates to a method for determining the need for antioxidant therapy for a patient, which comprises determining the presence of cells that contain ROS in a semen sample from said subject, using a method of the invention, and the percentage of cells that have DNA fragmentation using a method of the invention, characterized in that if the percentage of cells that comprise ROS and the percentage of cells that have DNA fragmentation are greater than said percentages in a reference sample, this is indicative that said patient should be treated with antioxidant therapy.

In a further aspect, the invention relates to a method for identifying a substance X with the capacity for decreasing the reactive oxygen species present in a cellular population that comprises:
 a) contacting said substance with said cellular population,
 b) contacting, in isotonic conditions, said biological sample with a thickening agent so that the motility of the cells of the cellular population is substantially reduced and with a compound that is an indicator of the presence of reactive oxygen species,
 c) maintaining the mixture obtained in step b) for a sufficient time for conversion of the indicator compound to a compound detectable in the presence of reactive oxygen species,
 d) putting the mixture obtained in c) with a gelling agent on a solid support in conditions suitable for gelling of the gelling agent to take place and
 e) quantifying the proportion of cells in which the detectable compound appears in which a decrease of the proportion of cells that show a change in coloration relative to the reference sample is indicative that substance X is capable of reducing the presence of reactive oxygen species in said cells.

In another aspect, the invention relates to a composition that comprises a thickening agent and a compound with the capacity to indicate the presence of ROS.

In another additional aspect, the invention relates to a kit that comprises a thickening agent, a compound that is an indicator of the presence of reactive oxygen species, an acid solution that denatures the DNA and a lysis solution that removes the nuclear proteins.

In another additional aspect, the invention relates to the use of a composition or of a kit that comprises a thickening agent and a compound that indicates the presence of ROS for determining the presence of reactive oxygen species in a cellular population.

In another aspect, the invention relates to the use of a kit that comprises a thickening agent, a compound that indicates the presence of ROS, an acid solution that denatures the DNA and a lysis solution that removes the nuclear proteins for determining the need for antioxidant therapy for a male subject.

DETAILED DESCRIPTION

First Method of the Invention

Figure 1:
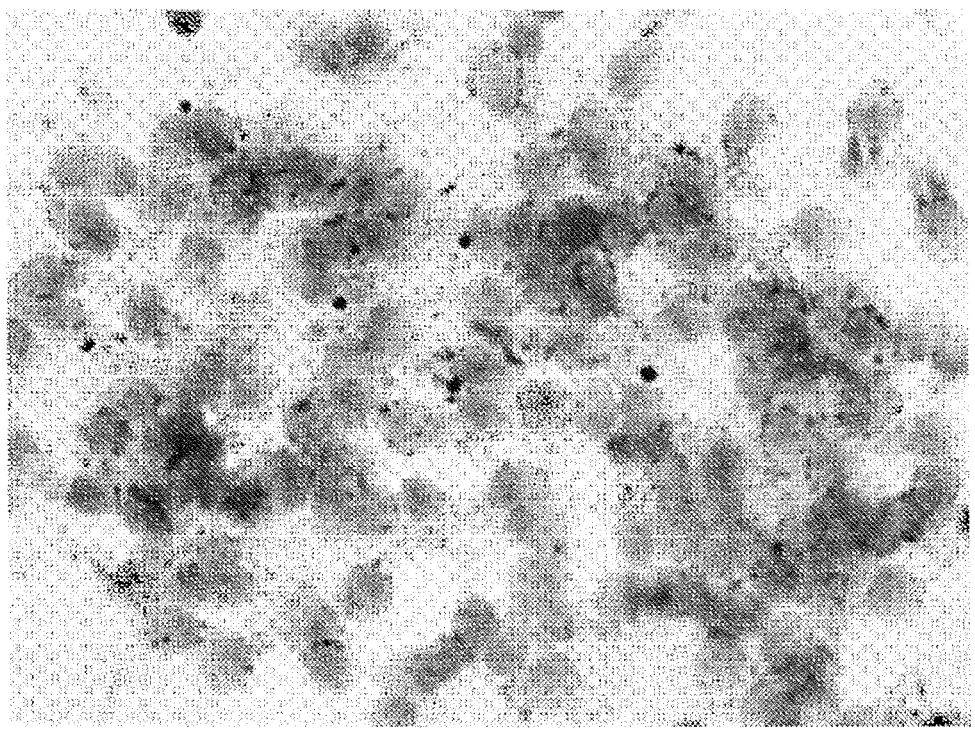
FIG. 1. Microscope image of sperm with NBT in liquid medium. It can be seen that the sperm tend to aggregate, so that the NBT positive sperm (that have ROS) can affect those that are NBT negative.

The present inventors have developed a method for determining the presence of cells that contain ROS in a cellular population in a biological sample. Thus, as can be seen in the example of the present invention, contacting a cellular population with an agent indicating the presence of ROS and in the presence of a viscosity-increasing agent makes it possible to detect those cells among the population that have ROS, avoiding the problems connected with the prior art resulting from aggregation of the cells.

Therefore, in a first aspect, the invention relates to a method (called first method of the invention hereinafter) for determining the presence of cells that contain ROS in a cellular population that comprises:
a) contacting, in isotonic conditions, said cellular population with a thickening agent so that the motility of the cells of the cellular population is substantially reduced and with a compound that indicates the presence of ROS,
b) maintaining the mixture obtained in step a) for a sufficient time for conversion of the indicator compound to a compound detectable in those cells that contain ROS,
c) putting the mixture obtained in b) with a gelling agent on a solid support in conditions suitable for gelling of the gelling agent to take place and
d) identifying those cells in which the detectable compound appears where the presence of the detectable compound in a cell is indicative of the presence of ROS in said cell.

"ROS" means the set of reactive molecules produced in some metabolic processes involving oxygen. They are very reactive molecules, owing to the fact that they possess unpaired electrons, which make them react with other organic molecules in redox processes. Examples of ROS are oxygen ions, free radicals and peroxides, among others.

"Cellular population" means, in the context of the present invention, cell cultures of eukaryotic cells, especially human cells, as well as populations of primary cells derived from the bone marrow, from blood, cells used in techniques of in vitro fertilization and the like. In a preferred embodiment, the cellular population is a population of sperm.

The term "sperm", as used in the present invention, refers to the reproductive cells of any male subject (man, ox, etc.). The population of cells can form part of a semen sample together with seminal fluid or diluted in a solution suitable for preserving the integrity of the sperm.

In a first step, the first method of the invention comprises contacting, in isotonic conditions, said cellular population with a thickening agent so that there is a substantial reduction in motility as well as sedimentation and aggregation of the cells of the cellular population and with a compound that is an indicator of the presence of reactive oxygen species.

"Isotonic conditions" refers to conditions in which, at equal temperature, two solutions have the same osmotic pressure, so that if said solutions are separated by a semipermeable membrane, there is no net flow of water through said membrane. "Osmotic pressure" means the pressure exerted by the particles of the solvent in a solution on the semipermeable membrane that separates it from another of higher concentration. Isotonic conditions are necessary for maintaining the integrity of the plasma membrane of the cell. Typical isotonic conditions comprise 285-315 mOsm/kg $H_2O$, depending on cell type.

The term "thickening agent" is used interchangeably with "viscosity-increasing agent" and refers to the compound that increases the internal resistance of a substance to flow when a constant stress is applied. As a result of the increase in resistance, the cells have less tendency to aggregate and moreover the cells moving in a mixture with said compound have lower motility. Thickening agents suitable for use in the present invention include, but are not limited to:
(i) polymers of carboxylic acids formed by crosslinked polymers formed from polymers of acrylic acid, substituted acrylic acid, salts and esters of acrylic acid and include compounds of the CAROPOL® family, including CAROPOL® of series 900 (for example, CAROPOL® 854), CAROPOL® #1342, CAROPOL® #1382, PEMULEN® TR-1 and PEMULEN® TR-2,
(ii) intermeshed polyacrylate polymers
(iii) polyacrylamide polymers and especially nonionic polyacrylamide polymers both linear and branched and formed from acrylamide and methacrylamide monomers substituted with one or two (C1-C5) alkyl groups. The preferred monomers include, but are not limited to, acrylamide, methacrylamide, N-methacrylamide, N-methylmethacrylamide, N,N-dimethylmethacrylamide, N-isopropylacrylamide, N-isopropylmethacrylamide and N,N-dimethylacrylamide. These polymers generally have a molecular weight above 1000000, preferably above 1500000 and up to 3000000. Preferred polymers of this category include SEPIGEL® 305 from Seppic Corporation (Fairfield, N.J.), Hypan SR150H, SS500V, SS500W, SSSA100H, from Lipo Chemicals, Inc. (Patterson, N.J.).
(iv) polysaccharides such as agarose, cellulose, carboxymethyl hydroxyethylcellulose, hydroxyethylcellulose, hydroxyethyl ethylcellulose, hydroxypropylcellulose, hydroxypropyl methylcellulose, methyl hydroxyethylcellulose, microcrystalline cellulose, cellulose sodium sulfate, and mixtures thereof. Celluloses substituted with alkyl groups, in which the hydroxyl groups of the celluloses are hydroxyalkylated (preferably hydroxyethylated or hydroxypropylated) to form hydroxyalkylated celluloses, which are then modified with a linear or branched C10-C30 chain via bonds of the ether type, can also be used. Examples of alkyl groups that are used for modifying the hydroxycelluloses include stearyl, isostearyl, lauryl, myristyl, cetyl, isocetyl, cocoyl, palmityl, oleyl, linoleyl, linolenyl, ricinoleyl, behenyl. Preferred hydroxycelluloses include cetyl hydroxyethylcellulose (NATROSOL® (3) CS Plus from Aqualon Corporation).
(v) gums including gums of acacia, agar, algin, alginic acid, ammonium alginate, amylopectin, calcium alginate, calcium carrageenan, carnitine, carrageenan, dextrin, gelatin, gellan gum, guar gum, hydroxypropyltrimonium chloride guar, hectorite, hyaluronic acid, chitosan, hydroxypropyl guar, karaya gum, kelp, locust bean gum, natto gum, potassium alginate, propylene glycol alginate, sclerotium gum, dextran carboxymethyl sodium, sodium carrageenan, gum tragacanth, xanthan gum and mixtures thereof.
(vi) intermeshed copolymers of vinyl ether and maleic anhydride such as PVM/MA.
(vii) crosslinked polymers of polyvinylpyrrolidones such as ACP-1120, ACP-1179, and ACP1 180, available from International Specialty Products (Wayne, N.J.).
(viii) thickening agents not included in any of the above groups, such as alginates; carbomers such as carbomers 934, 934P, 940 and 941; gum of cellulose, cetearyl alcohol, cocamide DEA, dextrin; gelatin; hydroxyethylcellulose; hydroxypropylcellulose; hydroxypropyl methylcellulose; magnesium and aluminum silicate, myristyl alcohol; oat flour; oleamide DEA; oleic alcohol; PEG-7M; PEG-14M; PEG-90M; stearamide DEA; stearamide MEA; wheat starch, xanthan gum and the like.

Step a) of the first method of the invention is carried out so that there is substantial reduction in the motility of the cells of the cellular population, preferably during the time that step a) is carried out. Substantial reduction in the motility of the cells of the cellular population means that the cells reduce their natural capacity for movement or displacement by at least 10%, 20%, 30%, 40%, 50%, 60%, 70%, 80%, 90% or 100%, in which case the cells do not move appreciably during the time that step a) is carried out. In the case when the cellular population under investigation is a population of sperm, a person skilled in the art can determine the conditions (concentration and temperature) in which a given thickening agent reduces cellular motility to values suitable for preventing cellular aggregation using widely known methods such as:

Colorimetric methods such as that marketed under the brand name Fertell in which the sample that contains sperm is heated to 37° C. and in which the motile sperm are detected on the basis of their ability to swim to a sensor coated with anti-CD95 antibodies conjugated with colloidal gold.

Colorimetric tests such as those described in WO 93/22053 and in U.S. Pat. No. 5,434,027.

Tests based on devices with microchannels in which the motile sperm reach a detector and in which detection is carried out using a fluorescent indicator that is captured by the sperm and converted to a detectable agent.

Methods based on visual inspection of sperm moving through a microchannel toward an oocyte.

Methods based on detection of changes in optical density of a sample due to the motility of the cells, as described in U.S. Pat. No. 4,176,953.

Methods based on detection of changes in the reception of acoustic waves caused by the passage of sperm through a microchannel as described in WO07085839A.

Step a) additionally comprises contacting the cellular population under investigation with an agent indicating the presence of ROS.

The term "ROS indicator", as used in the present invention, refers to any compound that in the presence of ROS undergoes a change in its properties so that it is detectable, either directly from some property of said compound or indirectly because said compound has the capacity to modify a second molecule that is detectable.

Preferred ROS indicators include tetrazolium salts, derivatives and analogs. The tetrazolium salts are compounds that have a tetrazole, tetrazolyl or tetrazolo structure. The tetrazolium salt is an organic salt that comprises one or two tetrazole rings and one or more substitutions with an aryl residue (phenyl or substituted phenyl) or naphthyl in different positions, preferably in positions 1, 2, 3 and 5. Typically, the tetrazolium salts that comprise two tetrazole rings are coupled so that they supply a diphenyl group or a naphthyl group, where the tetrazole groups are in the two para positions.

The compounds that in the presence of ROS undergo a change in their properties so that they are detectable, which can be used for carrying out the present invention, can be, among others, those shown in Table 1, described in U.S. Pat. No. 6,368,818.

TABLE 1

COMPOUNDS INDICATING THE PRESENCE OF ROS SUITABLE FOR USE ACCORDING TO THE INVENTION

| | | |
|---|---|---|
| I | pABT | p-Anisyl tetrazolium blue chloride |
| II | pApNBT | p-Anisyl chloride p nitro tetrazolium blue |
| III | BSPT (thiazolyl blue) | 2-2'-Benzothiazolyl-5-styryl-3-(4'-phthalhydrazidyl) tetrazolium chloride |
| IV | BT also called tetrazolium blue chloride | 2-[4-[4-(3,5-Diphenyltetrazol-2-ium-2-yl)-3-methoxyphenyl]-2-methoxyphenyl]-3,5-diphenyltetrazol-2-ium dichloride |
| V | BTSPT | 2-(2'-Benzothiazolyl)-5-styryl-3-(4'-phthalhydrazidyl)-tetrazolium chloride |
| VI | CTC | 5-Cyano-2,3-ditolyl tetrazolium chloride |
| VII | DMDPT | [3-4,s-Dimethylthiazol-2-yl)-2,5-diphenyl] tetrazolium bromide or 1-[4,5-dimethylthiazol-2-yl]-2,5-diphenyltetrazolium bromide |
| VIII | DSNBT (distyrylnitroblue tetrazolium chloride) | |
| IX | (1H)-tetrazole | |
| X | IDNTT iodonitrotetrazolium chloride | 2-(4-Iodophenyl)-3-(4-nitrophenyl)-5-phenyltetrazol-2-ium chloride |
| XI | INT (Nitro Tetrazolium Violet chloride) | p-iodo violet nitrotetrazolium (2-(4-iodophenyl)-3-(4-nitrophenyl)-5-phenyltetrazolium |
| XII | INpT | 2-(p-iodophenyl)-p-nitrophenyl-5-phenyltetrazolium chloride |
| XIII | Mnbt (m-Nitro blue Tetrazolium chloride) | |

TABLE 1-continued

COMPOUNDS INDICATING THE PRESENCE OF ROS SUITABLE
FOR USE ACCORDING TO THE INVENTION

| | | |
|---|---|---|
| XIV | mNNT (m-Nitro Neotetrazolium chloride) | |
| XV | MNSTC | 2,2-bis(2-methoxy-4-nitro-5-sulfophenyl)-2H-tetrazolium-5-carboxanyl |
| XVI | MTS | 3-(4,5-dimethylthiazol-2-yl)-5-(3-carboxymethoxyphenyl)-2-(4-sulfophenyl)-2H-tetrazolium salt |
| XVII | MTT (Tetrazolium bromide or thiazolyl blue tetrazolium bromide) | 3+4,5-dimethylthiazol-2-yl-2,s-diphenyltetrazolium bromide |
| XVIII | NBMT (Nitro blue Monotetrazolium chloride) | |
| XIX | NBT (p-Nitro Blue Tetrazolium Chloride or Nitro blue tetrazolium chloride) | (2,2'-dinitrophenyl-5,5'-diphenyl-3,3'-(3,3'-dimethoxy-4,4'-diphenylene)ditetrazolium chloride |
| XX | NT (Neotetrazolium chloride) | 2,2',5,5'-Tetraphenyl-3,3'(p-diphenylene)ditetrazolium chloride |
| XXI | NTV (Nitrotetrazolium Violet) | |
| XXII | Thiazolyl blue | 2-(3,5-diphenyltetrazol-2-ium-2-yl)-4,5-dimethyl-1,3-thiazole bromide |
| XXIII | TB (tetrazolium blue chloride) | [(3,3'-dimethoxy (1,1'-biphenyl)-4,4'-dilyl]bis(2,5-diphenyl-2H-tetrazolium) dichloride |
| XXIV | oTTR (o-Tolyl Tetrazolium Red) | 2-(2-Methylphenyl)-3,5-diphenyltetrazol-2-ium chloride |
| XXV | PCTMB | sodium 3'-[1-[(phenylamino)-carbonyl]-3,4-tetrazolium bis(4-methoxy-6-nitro)benzene-sulfonic acid hydrate |
| XXVI | PNBT (p-Nitro Blue Tetrazolium chloride) | 2-[2-methoxy-4-[3-methoxy-4-[3-(4-nitrophenyl)-5-phenyltetrazolidin-2-yl]phenyl]phenyl]-3-(4-nitrophenyl)-5-phenyltetrazolidine |
| XXVII | PTB (Piperonyl tetrazolium blue) | |
| XXVIII | pTTR (p-Tolyl Tetrazolium red) | 2-(4-Methylphenyl)-3,5-diphenyltetrazol-2-ium chloride |
| XXIX | TC-NBT (Thiocarbamyl nitro blue tetrazolium chloride) | (2,2'-di-p-Nitrophenyl-5,5'-di-p-thiocarbamylphenyl-3,3'[3,3'-dimethoxy-4,4'-biphenylene]ditetrazolium chloride |
| XXX | TNBT (Tetranitroblue tetrazolium chloride) | 2-[4-[4-[3,5-bis(4-nitrophenyl)tetrazol-2-ium-Dichloride 2-yl]-3-methoxyphenyl]-2-methoxyphenyl]-3,5-bis(4-nitrophenyl)tetrazol-2-ium |
| XXXI | TPTT (1,3,5-triphenyltetrazolium) | |
| XXXII | TR (TTC or TPT or tetrazolium red) | 2,3,5-Triphenyltetrazolium chloride |
| XXXIII | TV (Tetrazolium violet or Violet Tetrazolium) | 2,3,5-Triphenyl-2-H-Tetrazolichloride, 2,5-diphenyl-3-[alpha-naphthyl]-tetrazolium chloride, 2,5-diphenyl-3-[1-naphthyl]-2H-tetrazolium chloride |
| XXXIV | VTB (Veratryl tetrazolium blue) | |
| XXXV | WST-1 | 4-[3-(4-Iodophenyl)-2-(4-nitrophenyl)-2H-5-tetrazolium]-1,3-benzene disulfonate |
| XXXVI | XTT | 2,2-bis(2-Methoxy-4-nitro-5-sulfophenyl)-2H-tetrazolium-5-carboxanilide |

In step b) of the first method of the invention, the mixture obtained in step a) is maintained for a time sufficient for the compound that indicates the presence of ROS to be transformed into a compound detectable in those cells that contain said ROS. In the case when the agent indicating the presence of ROS is NBT, step b) is carried out for the time required for said NBT to be reduced to give rise to formazan. Said process can be monitored conveniently by detection of the absorbance at 630 nm. In a preferred embodiment, the reaction is maintained for at least 5, 10, 15, 20, 25, 30, 35, 40, 45, 50, 55, 60 minutes or for at least 2, 3, 4, 5, 6, 7, 8, 9 or 20 hours. The reaction temperature is typically 37° C., although it can be carried out at temperatures in the range 20-45° C., preferably 25-40° C., even more preferably in the range 30-40° C.

In a preferred embodiment, the first method of the invention comprises an additional step (step b2) after step b), in which the concentration of the detectable compound in the sample is determined, where an increase in the concentration of said compound relative to a reference sample is indicative of the presence of reactive oxygen species in said cellular population. In this way, in addition to direct identification of the number of cells that comprise the detectable compound, a value of absorbance is obtained that is indicative of the presence of reactive oxygen species in said cellular population.

A person skilled in the art will appreciate that determination of the concentration of the detectable compound can be performed in an absolute manner, i.e. by determining the concentration of the compound in the sample, or relatively, i.e. by determining the relation between the concentration of the detectable compound in the sample and in the reference sample.

In a preferred embodiment, the detectable compound is a colored compound, and therefore the concentration of said compound is measured by determining the absorbance of said compound at the appropriate wavelength.

"Absorbance" or optical density as used in the present invention refers to the proportion of incident light that is absorbed by a substance. The absorbance of a sample can be determined, for example, with a spectrophotometer. In a preferred embodiment, the indicator of ROS is NBT, in which case determination of the concentration of the compound is carried out by measuring the absorbance of the sample in step b2) at 630 nm.

"Reference sample" means a cellular population that lacks ROS or that has been treated to remove the ROS. In a preferred embodiment, when the cellular population that is under investigation is a population of sperm, it is possible to use a population of sperm from a fertile subject as the reference sample. "Fertile subject" means a subject whose sperm are capable of fertilizing an oocyte. The WHO criteria for regarding a subject as fertile is a quantity of 10 million motile sperm per milliliter of semen.

In a preferred embodiment, the method of the invention includes an additional step after step b) (step b3) that can be carried out in parallel with step b2) for determining the presence of DNA fragmentation and that comprises incubating a sample of the mixture from step b) in suitable conditions for denaturation of the DNA to occur and for determining the appearance of halos around the head of the sperm, wherein the presence of halos below a certain threshold value is indicative that the sperm have DNA fragmentation.

The presence of halos around the head of the sperm can be detected essentially by contacting a fraction of the cells of the sample with an acid solution and with a lysis solution. The treatment with the acid solution denatures the DNA. Then it is treated with a lysis solution, which removes most of the nuclear proteins. After this treatment, the sperm with fragmented DNA do not show halos, whereas those sperm in which the DNA is intact develop large halos around the nucleoid.

The term "acid solution", as used in the present invention, refers to any solution, suspension, emulsion or other fluid that contains a compound that acts as a donor of H+ groups. In a preferred embodiment, the acid solution can contain an acid selected from the group hydrochloric, acetic, nitric acid or mixtures thereof, among others. In an even more preferred embodiment, the acid solution contains hydrochloric acid between 0.04 and 0.08 M.

The term "lysis solution", as used in the present invention, refers to any solution, suspension, emulsion or other fluid that is capable of causing lysis of cells that have been contacted with said solution. The lysis solution can contain at least one detergent, at least one chaotropic agent and/or at least one reducing agent. Detergents suitable for use in the denaturing solution include, but are not limited to, anionic detergents (for example sodium lauryl sulfate, ammonium lauryl sulfate), cationic detergents (trimethylammonium cetyl bromide, cetylpyridinium chloride, benzalkonium chloride, benzethonium chloride and the like), zwitterionic detergents (for example CHAPS, lecithins) or nonionic detergents (cetyl alcohol, stearyl alcohol, oleyl alcohol, decyl glucoside, lauryl glucoside, octyl glucoside, Tritium X-100). In a preferred embodiment, the detergent that forms part of the lysis solution is Triton X-100. In an even more preferred embodiment, the detergent that forms part of the lysis solution is sodium lauryl sulfate (SDS), preferably at 1%.

Chaotropic agents for use in the present invention include, but are not limited to, urea (typically at a concentration of 6-8 M), thiourea (typically at a concentration of at least 2 M), guanidinium chloride (typically at a concentration of at least 6 M) and lithium perchlorate (typically at a concentration of at least 4.5 M).

Reducing agents suitable for use in the present invention include, but are not limited to, beta-mercaptoethanol, dithiothreitol and tris(2-carboxyethyl)phosphine. In a preferred embodiment, the reducing agent is dithiothreitol, preferably at 0.8 M.

In a preferred embodiment, the analytical method is carried out as described by Fernández J L. et al., (Fertil. Steril. 2005; 84: 860) and consists of immersing the sperm obtained from samples that are fresh, frozen or diluted in an agarose gel whose support comprises a pretreated slide and in which the sample is treated successively with a denaturing acid solution (0.08 N HCl), a first neutralizing lysis solution (0.4 M Tris, 0.8 M DTT, 1% SDS, and 50 mM EDTA, pH 7.5), a second neutralizing lysis solution (0.4 M Tris, 2 M NaCl, and 1% SDS, pH 7.5). Detection of the DNA halos is performed visually after staining the sperm with a DNA probe, preferably a fluorescent probe, and even more preferably DAPI.

In a preferred embodiment, the sample is considered to be fertile when at least 20-30% of the sperm have a halo larger than or equal to 7.5 μm. Determination of the halo is carried out typically by direct visualization of the sperm by phase contrast microscopy.

Methods for determining whether a solution is suitable for use in the acid treatment of the present invention comprise analyzing whether said solution is capable of denaturing DNA. Said capacity can be analyzed using various techniques known in the prior art, such as the increase in absorbance at 260 nm, among others.

Methods for determining whether a lysis solution is suitable for use in the present invention comprise analyzing the capacity of said solution for removing nuclear proteins of DNA. Said capacity can be analyzed using various techniques widely known in the prior art, including DNase I footprinting, testing for change of motility in gel, nitrocellulose binding assay, Western blot, among others.

Step c) of the first method of the invention comprises putting the mixture obtained in b) with a gelling agent on a solid support in conditions suitable for gelling of the gelling agent to take place.

"Gelling agent" means a substance that permits coagulation of a colloidal solution in the bulk by formation of an extremely fine solid network that contains a liquid in its mesh.

In a preferred embodiment, the thickening compound used in step a) of the first method of the invention is at the same time a gelling compound, so that step c) does not require addition of a gelling compound but simply a change of conditions so that the thickening/gelling compound gels so that the cells of the cellular population are immobilized.

Gelling and viscosity-increasing agents that can be used in the present invention are selected from Table 2.

TABLE 2

GELLING AND VISCOSITY-INCREASING COMPOUNDS SUITABLE FOR USE ACCORDING TO THE INVENTION

| | |
|---|---|
| I | Agarose, polysaccharide formed by alpha and beta galactoses that is extracted mainly from algae of the genera *Gelidium* and *Gracilaria*. |
| II | Alginic acid, product obtained from various types of algae, including *Macrocystis*, *Fucus*, *Laminaria*. |
| III | Alginate and derivatives thereof, among which we may mention in particular sodium, potassium, ammonium, calcium, and propylene glycol alginate. |
| IV | Agar, extracted from several types of red algae, including those of the genus *Gelidium*. |
| V | Carrageenans, product obtained from several types of algae: *Gigartina*, *Chondrus*, *Furcellaria* and others. |
| VI | Locust bean gum, product extracted from the seeds of *Ceratonia siliqua* |
| VII | Guar gum extracted from *Cyamopsis tetragonolobus* |
| VIII | Gum tragacanth, exudate from the tree *Astrogalus gummifer* |
| IX | Gum arabic, exudate from the tree *Acacia senegalia* |
| X | Xanthan gum, produced by *Xanthomonas campestris* |
| XI | Karaya gum, exudate from the tree *Sterculia urens* |
| XII | Tara gum, extracted from the seeds of *Caesalpinia spinosa* |
| XIII | Gellan gum, produced by *Pseudomonas elodea* |
| XIV | Sorbitol and sorbitol syrup |
| XV | Mannitol |
| XVI | Esters of fatty acids and sorbitan, among which we may mention in particular polyoxyethylene sorbitan monolaurate, polyoxyethylene sorbitan monooleate, polyoxyethylene sorbitan monopalmitate, polyoxyethylene sorbitan monostearate, polyoxyethylene sorbitan tristearate |
| XVII | Pectin, a major constituent of plant cell walls |
| XVIII | Ammonium phosphatides |
| XIX | Sucrose acetate isobutyrate |
| XX | Glyceride esters of wood rosin |
| XXI | Cellulose and derivatives, among which we may mention in particular microcrystalline cellulose, methylcellulose, hydroxypropylcellulose, hydroxypropylmethyl cellulose |

A person skilled in the art will appreciate that the conditions suitable for gelling of the thickening agent will depend on the nature of the latter. Thus, in the preferred case when agarose is used as thickening agent in step a) and as gelling agent in step c), it is sufficient to lower the temperature below the gelling temperature of agarose at the concentration at which the latter is present. Said temperature can easily be determined by a person skilled in the art from tables in which the gelling temperature of the agarose is correlated with the concentration in the sample (for example, the table available at http://www.lonzabio.com/uploads/tx_mwaxmarketingmaterial/Appendix_B_-_Agarose_Physical_Chemistry.pdf). In a preferred embodiment, the thickening/gelling agent is a low melting point agarose.

Agaroses of low melting point are available commercially, such as Ultra Pure® agarose (Invitrogen), NuSieve® GTG® Agarose (Lopza), LM Agarose and LM Sieve (Pronadisa), Agarose SERVA Premium (Serva) and the like. In the case when the gelling agent is agarose, step c) is carried out by raising the temperature of the mixture to 10-30° C., preferably 15-25° C., even more preferably 20-25° C.

In the case when the gelling agent is alginate, gelling is induced by adding calcium ions to the medium.

"Solid support", as used in the invention, refers to a surface of glass, plastic, ceramic or metal among others, for holding the mixture of the invention that contains the gelling agent. Depending on the method used in quantification of the cells, it will be necessary for said support to allow light to pass through. Preferably the solid support is a slide.

In a preferred embodiment, step c) is carried out using agarose at a concentration of 0.5-5%, in which case gelling is carried out directly on the slide by application of the mixture obtained in step b) on a slide and incubation at room temperature.

Finally, step d) of the first method of the invention comprises identifying those cells in which the detectable compound appears, so that said cells will be those that contain ROS. In a preferred embodiment, the cells that comprise the detectable compound resulting from conversion of the indicator of ROS are detected by direct observation by optical microscopy. In the case when the indicator compound is a tetrazolium salt, preferably NBT, the detectable compound (formazan precipitate) appears as a precipitate of a deep blue color normally localized on the intermediate portion and head of the sperm.

Although the various cells in the sample can be identified by phase contrast microscopy, it is preferable to stain the cells with a dye. Typically, staining is carried out after the step of gelling of the gelling agent. Staining solutions that can be used for carrying out the present invention include, but are not limited to, Gomori trichrome, Masson trichrome, methylene green, Giemsa, Wright, hematoxylin-eosin, methylene blue, among others. In a preferred embodiment, the cells are stained with methylene green.

Second Method of the Invention

The present inventors have developed a method for determining the need for antioxidant therapy of a patient that comprises determining the presence of cells that contain ROS in a semen sample from said subject using a method of the invention, and the percentage of cells that have DNA fragmentation using a method of the invention, wherein if the percentage of cells that comprise ROS and the percentage of cells that have DNA fragmentation are greater than said percentages in a reference sample it indicates that said patient should be treated with antioxidant therapy.

"Antioxidant therapy", as used in the present invention, refers to the administration of antioxidants for treating a disease. "Antioxidant" means all those elements whose function is to remove free radicals from the body. Several studies have demonstrated the effect of treatment with antioxidants in reducing sperm DNA fragmentation (Greco E. et al., J. Androl. 2005, 26: 349-53). Among the antioxidant treatments that can be administered to patients who have a high percentage of cells that comprise ROS and sperm DNA fragmentation, we may mention in particular the administration of suitable doses of vitamin E, C, L-carnitine, beta-carotene, flavonoids, lycopene, copper, zinc, manganese, iron and selenium among others.

As used here, the term "determination" refers to determination of the probability that the patient needs to be given antioxidant therapy. As will be understood by persons skilled in the art, prediction of the need for said antioxidant therapy, although it should preferably be correct, does not have to be correct for 100% of the subjects to be diagnosed or evaluated. A person skilled in the art can easily determine whether the result obtained for a subject is statistically significant using various tools for statistical evaluation that are well known, for example determination of confidence intervals, determination of p values, Student's t test, Mann-Whitney test, etc. The details can be found in Dowdy and Wearden, Statistics for Research, John Wiley & Sons, New York 1983. The preferred confidence intervals are at least 50%, at least 60%, at least 70%, at least 80%, at least 90%, at least 95%. The p values are preferably 0.2, 0.1 or 0.05.

"Quantify the proportion of cells" as used here refers to expressing numerically the cells that show the detectable compound relative to the cells that do not show said compound. In a particular embodiment, said method is carried out by optical microscopy.

"Reference sample" means, in the context of the present invention, the biological sample of a fertile subject or previous samples from the same individual, which are used for determining the presence of ROS.

The second method of the invention envisages the possibility of determining the need for antioxidant therapy of a subject from the various results supplied by the first method of the invention. Thus, an indication of the existence of the need for antioxidant therapy is the existence of a percentage of cells that show ROS above a defined threshold value. Said value can be combined with the presence of a percentage of cells that do not show halos above a defined threshold value. Thus, the second method of the invention makes it possible to determine the possibility that a subject needs antioxidant therapy if:

in a semen sample from said subject, there is a percentage of cells that contain ROS above a threshold value. In a preferred embodiment, the threshold value of the percentage of cells that contain ROS is 20%. Alternatively, if the sample has been treated with gradients of PERCOLL®, the threshold value is 30% and/or in a semen sample from said subject there is a percentage of cells that contain ROS above a threshold value and the percentage of cells that do not show halos is above a threshold value. In a preferred embodiment, the threshold value of the percentage of cells that contain ROS is 20%. Alternatively, if the sample has been treated with gradients of PERCOLL®, the threshold value is 30%. In a preferred embodiment, the threshold value of the percentage of cells that do not show halos is 20%.

Threshold values for each of the parameters that are obtained on applying the various embodiments of the first method of the invention can be determined from a reference sample.

The terms and expressions "cell", "cellular population", "isotonic conditions", "thickening agent", "compound indicating the presence of reactive oxygen species" and "gelling agent" were defined in detail in the context of the first method of the invention and are used in the same way in the second method of the invention.

Third Method of the Invention

The present inventors have developed a method (hereinafter: third method of the invention) for identifying a substance (hereinafter substance X) with capacity for decreasing the ROS present in a cellular population. Thus, in another aspect, the invention relates to a method (hereinafter: third method of the invention) that comprises:

a) contacting said substance X with said cellular population, b) contacting, in isotonic conditions, said cellular population with a thickening agent so that the motility of the cells of the cellular population is substantially reduced and with a compound that is an indicator of the presence of reactive oxygen species, c) maintaining the mixture obtained in step b) for a sufficient time for conversion of the indicator compound to a compound detectable in the presence of reactive oxygen species, d) putting the mixture obtained in c) with a gelling agent on a solid support in conditions suitable for gelling of the gelling agent to take place and e) quantifying the proportion of cells in which the detectable compound appears wherein a decrease of the proportion of cells that show a change in coloration relative to the reference sample is indicative that substance X is capable of reducing the presence of reactive oxygen species in said cells;

wherein the decrease in the proportion of cells that show a change in coloration is indicative that substance X is capable of reducing the presence of ROS in said cells.

A person skilled in the art will understand that on occasions previous treatment with an agent that generates free radicals will be necessary in order to observe the effect of the antioxidant. Compounds that can be used for generating free radicals include hydrogen peroxide, among others.

In a first step, the third method of the invention comprises contacting the cellular population with a compound or preparation whose effect. "Contacting" a cell with the candidate compound includes, according to the present invention, any possible form of bringing the candidate compound into the cell that expresses the DNA construct. Thus, in the case when the candidate compound is a molecule of low molecular weight, it is sufficient to add said molecule to the culture medium. In the case when the candidate compound is a molecule of high molecular weight (for example, biopolymers such as a nucleic acid or a protein), it is necessary to provide the means for this molecule to enter the cell. In the case when the candidate molecule is a nucleic acid, conventional methods can be used for transfection, as described above for introducing the DNA construct. In the case when the candidate compound is a protein, the cell can be contacted both with the protein directly and with the nucleic acid that encodes it, coupled to elements that permit its transcription/translation once inside the cell. For this, any of the methods mentioned above to enable them to enter the cell can be used. Alternatively, it is possible to contact the cell with a variant of the protein that is to be investigated that has been modified with a peptide that is capable of promoting the translocation of the protein inside the cell, such as the Tat peptide derived from the TAT protein of HIV-1, the third helix of the homeodomain of the Antennapedia protein of *D. melanogaster*, the VP22 protein of the herpes simplex virus and oligomers of arginine (Lindgren, A. et al., 2000, *Trends Pharmacol. Sci.*, 21: 99-103, Schwarze, S. R. et al., 2000, *Trends Pharmacol. Sci.*, 21: 45-48, Lundberg, M. et al., 2003, *Mol. Therapy.* 8: 143-150 and Snyder, E. L. and Dowdy, S. F., 2004, *Pharm. Res.* 21: 389-393).

Preferably, the test compound is not isolated but forms part of a more or less complex mixture either derived from a natural source or forming part of a library of compounds. Examples of libraries of compounds that can be tested according to the method of the present invention include, but are not limited to, libraries of peptides including both peptides and peptide analogs that comprise D-amino acids or peptides that comprise nonpeptide bonds, libraries of nucleic acids including nucleic acids with non-phosphodiester bonds of the phosphorothioate type or peptide nucleic acids, libraries of antibodies, of carbohydrates, of low molecular weight compounds, preferably organic molecules, of peptidomimetics, and the like. In the case when a library of organic compounds of low molecular weight is used, the library can have been preselected to contain compounds that can enter the cell more easily. Thus, the compounds can be selected on the basis of certain parameters such as size, lipophilicity, hydrophilicity, and capacity for forming hydrogen bridges.

Alternatively, the test compounds can form part of an extract obtained from a natural source. The natural source can be animal or vegetable obtained from any environment, including, non-exhaustively, extracts from land, aerial, marine organisms and the like.

Steps b) to e) coincide essentially with steps a) to d) of the first method of the invention and the terms used in said method are used with the same meaning in the third method of the invention.

In the case when the candidate compound forms part of a more or less complex mixture, the invention additionally comprises one or more steps of fractionating said mixture and repetition of steps (a), (b), (c), (d) and (e) of the method of the invention a variable number of times until the compound of the mixture responsible for the decrease in level of ROS has been isolated. Methods for fractionation of compounds present in a mixture include chromatography (thin-layer, gas or gel molecular exclusion, affinity), crystallization, distillation, filtration, precipitation, sublimation, extraction, evaporation, centrifugation, mass spectrometry, adsorption and the like.

In a particular embodiment of the third method of the invention, additionally a step c2) is included, which comprises determining the concentration of the detectable compound in the mixture from step c) and wherein a decrease in absorbance relative to a reference sample is indicative that substance X is capable of reducing the presence of ROS in said cellular population.

In another particular embodiment of the third method of the invention that additionally comprises a step d2) that comprises incubating a sample of the mixture from step c) with a denaturing solution, and then a lysis solution and finally staining said cells, wherein the cells that do not show halos with a size above a defined threshold value are indicative that said cells have fragmented DNA.

Compositions and Kits of the Invention and Diagnostic Uses Thereof

In another aspect, the invention relates to a composition that comprises a gelling agent and a compound that indicates the presence of ROS.

The term "composition", as used in the present invention, refers to a mixture of two or more components. In the case of the present invention, the compositions of the invention contain the necessary reagents for determining the need for antioxidant therapy of a subject from a semen sample from said subject. Preferably, the composition of the invention comprises a thickening agent (preferably agarose and even more preferably low melting point agarose) and an indicator of ROS (preferably a tetrazolium salt and even more preferably NBT) wherein both components form a mixture. In a preferred embodiment, the compositions of the invention comprise agarose at a concentration from 2% to 5% and NBT at a concentration of up to 1 mg/ml.

The terms "thickening agent", "agent indicating the presence of ROS" and "ROS" were defined above in the context of the first method of the invention.

In a preferred embodiment, the thickening compound is, moreover, a gelling compound, the thickening/gelling compound is agarose and the agarose is low melting point agarose.

In another preferred embodiment, the compound indicating the presence of reactive oxygen species is a tetrazolium salt, and even more preferably it is NBT.

In another preferred embodiment of the composition of the invention, the thickening compound is low melting point agarose, the compound indicating ROS is NBT, the agarose is present at a concentration from 2% to 5% and NBT is present at a concentration of up to 1 mg/ml.

In another additional aspect, the invention relates to a kit that comprises a gelling agent, a compound that is an indicator of the presence of reactive oxygen species, an acid solution and a lysis solution. The terms "acid solution" and "lysis solution" were explained in detail in the context of the first method of the invention and apply in the same way to the kit of the invention. In a preferred embodiment, the kit of the invention additionally comprises a probe for detection of DNA, preferably a fluorescent probe (ethidium bromide, acridine orange, propidium iodide, ToPro-3, DAPI), and even more preferably DAPI.

In another additional aspect, the invention relates to the use of a composition or of a kit that comprises a gelling agent and a compound with capacity for forming a product detectable in the presence of ROS for determining the presence of ROS in a cellular population.

In another additional aspect, the invention relates to the use of a composition or of a kit that comprises a gelling agent and a compound with capacity for forming a product detectable in the presence of ROS for determining the need for antioxidant therapy for a male subject.

The term "kit", as used in the present invention, refers to a combination of articles that facilitate the practical application of a process, method, test, analysis or manipulation of a sample. In the case of the present invention, the kits of the invention contain the reagents required for determining the need for antioxidant therapy of a subject from a semen sample from said subject. Preferably, the kit of the invention comprises a thickening agent (preferably agarose and even more preferably low melting point agarose) and an indicator of ROS (preferably a tetrazolium salt and even more preferably NBT) wherein both components are in one and the same container or in separate containers. Additional components that can form part of the kit of the invention include:

Suitable reagents for denaturation of DNA (acid solutions) and the reagents for removing the nuclear proteins (lysis solution).

Suitable reagents for staining the sperm, preferably methylene green.

The terms "thickening agent", "gelling agent", "ROS" and "compound with capacity for forming a product detectable in the presence of ROS" have already been defined.

The invention is now described in detail on the basis of the following examples, which are to be regarded as merely illustrative and not limiting the scope of the invention.

Example 1

The method of the present invention for determining the presence of ROS in a cellular population is an indirect method that has been correlated with other methodologies based on chemiluminescence (Esfandiari N. et al., J. Androl. 2003 November-December; 24(6): 862-70). Its main advantages are that it is very economical and only requires a light microscope.

Preparation of the Reagents

NBT is a water-soluble yellow salt that reacts in the presence of superoxide anions within cells producing a blue precipitate of diformazan. The quantity of diformazan crystals present in the cells reflects the production of superoxide ion by said cells.

For carrying out the method of the invention, first a mixture of agaroses and NBT (agaroses-NBT) was prepared. For this, 10 mg of NBT (Sigma N5514-10 tab) was dissolved in 10 ml of distilled water and the solution was maintained at 37° C. Separately, an amount of low melting point agarose between 2% and 5% was dissolved in PBS at pH 7 and it was left on a heating plate at 37° to prevent gelling. Next the two solutions were mixed in equal volumes and then distributed in volumes of 100 µl in Eppendorf tubes. The resultant mixture is stable between 2° C. and 22° C.

NBT Reaction

The semen sample was diluted in PBS to a concentration of between 5 and 10 million sperm per milliliter. The agaroses-NBT were put in a float and were incubated for 5 minutes in a bath in the range 90-100° C. until the agaroses dissolved. Alternatively a microwave could be used for melting the agarose. Then the tubes were transferred to a bath at 37° C. and were left for temperature adjustment for 5 minutes. A volume of semen (with the concentration adjusted) was mixed with an equal volume of agarose and was homogenized using a micropipette. The mixture was incubated at 37° C. for 45 minutes. In this time, the maximum of precipitated product (diformazan) is produced. During incubation, it is possible to collect a volume of 25 µl for determining DNA fragmentation according to the Halosperm kit (Halotech, S.L; Madrid).

During incubation, the mixture may assume a blue coloration, the intensity of which will depend on the presence of superoxide ion, both in sperm and in leukocytes present and in the seminal fluid. The intensity of coloration can be determined by measuring the absorbance at 630 nm in a spectrophotometer, cytometer or in a plate reader. This change of coloration gives a first indication of the presence of oxidative stress or deficiency in the detoxifying capacity of the sample.

For determining the percentage of sperm or cells present in the sample that are producing ROS, 10 µl of sample was collected for the purpose of incubation and was put on a pretreated slide. A cover slip was put on so that the agarose was spread, and it was left to gel at 4° C. for five minutes. At the end of this time, the cover was carefully removed and the agarose was left to dry in the air.

Then it was stained with a solution of methylene green for 5 minutes. To prepare this solution, 0.15 g of methylene green (Sigma s580104 50 mg) was weighed and was dissolved in 50 ml of distilled water, 25 µl of glacial acetic acid was added and stirred. After incubating the samples with the staining solution, they were washed in running water and were left to dry in the air. They are stored at room temperature.

Finally, they were mounted with DPX and 200 sperm were analyzed by direct observation in the light microscope, determining the proportion of cells that have ROS.

When the test is carried out in the absence of agarose, the sperm sediment or may interact physically with other sperm. Contact of sperm that have ROS with those that do not have them could trigger the production of diformazan in those which in principle are not producing reactive oxygen species and moreover quantification by optical microscopy is more difficult (FIG. 1).

The incorporation of agarose in suitable concentrations prevents sedimentation and unwanted contact between sperm that could produce artefacts in the results.

Figure 2:
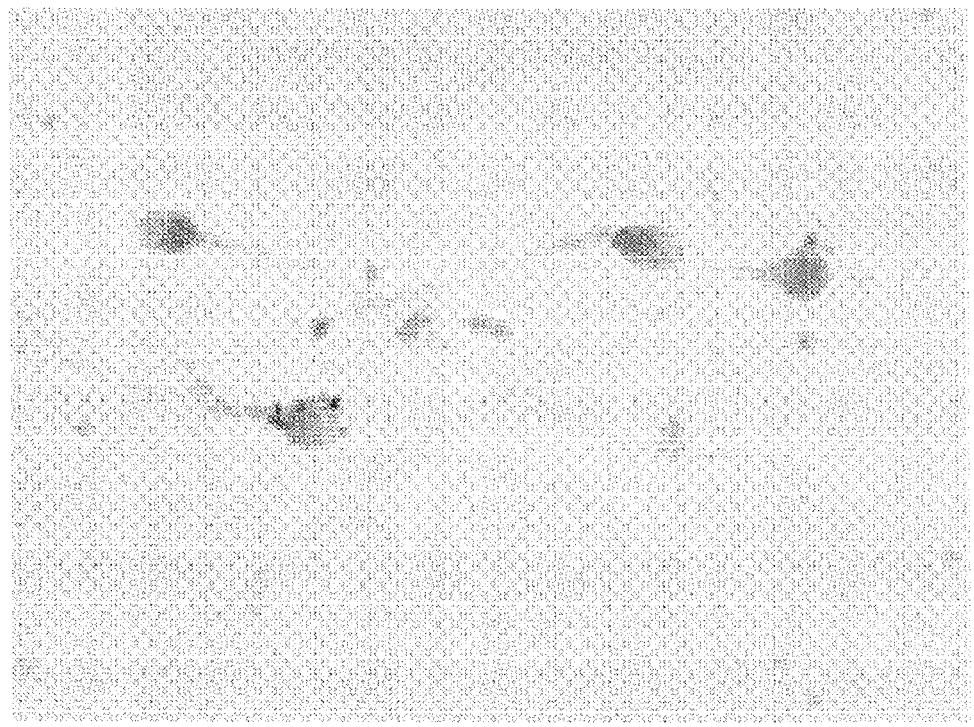
FIG. 2. Microscope image of NBT positive sperm. They have a precipitate of deep blue color normally located on the intermediate portion and the head.

Thus, when agarose-NBT is used, in NBT positive sperm that have ROS, some dark blue precipitates were observed, mainly located in the intermediate zone and head of the sperm (FIG. 2).

Figure 3:
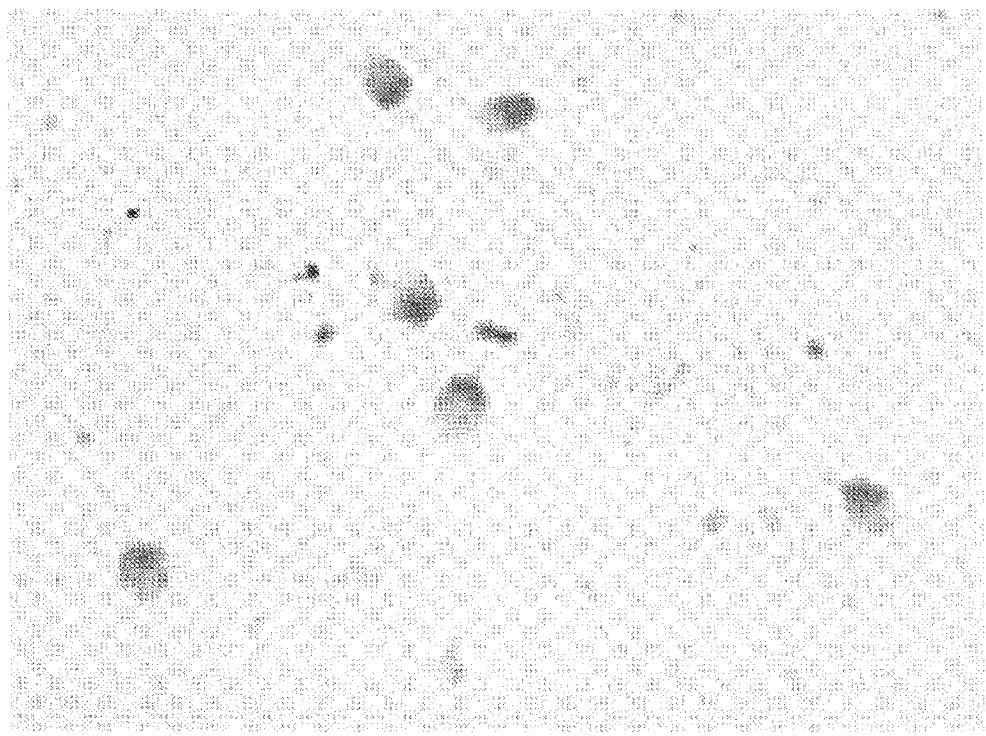
FIG. 3. Optical microscope image of an extension of human sperm immersed in agarose, negative for NBT, that do not have ROS.

Said precipitates are not observed in the NBT negative sperm (FIG. 3).

At the end of the process, the following information is obtained: 1) a value for sperm DNA fragmentation, 2) the proportion of NBT positive sperm and 3) a color change of the sample that represents a qualitative value (negative, slight, moderate, intense) or quantitative value (after measuring its absorbance) which can be compared with that of a reference sample.

Example 2

Comparative Study of the Agaroses of the Halosperm Kit and the Agaroses Modified with NBT The incorporation of agaroses modified with NBT for determining the presence of ROS in semen samples should not affect the efficacy of the fragmentation test of the Halosperm commercial kit. The purpose of the present study was to determine the effect of the agaroses-NBT on the result of the fragmentation test of the Halosperm kit.

For this, 8 different semen samples were analyzed from patients with infertility and who had an altered semen analysis. The variables investigated were SDF (sperm DNA fragmentation) which determines the percentage of sperm with fragmented DNA and DS (degraded sperm), which indicates the percentage of degraded sperm.

8 semen samples were analyzed from different patients with an altered semen analysis.

Then the data were analyzed statistically. Table 3 shows the descriptive statistics of the samples for the variables SDF and DS.

TABLE 3

| | | Descriptive statistics of the samples | | | |
|---|---|---|---|---|---|
| | Type | | | Statistic | Standard error |
| SDF | Normal agaroses | Mean | | 34.1875 | 5.77397 |
| | | Confidence interval for the mean at 95% | Lower limit | 20.5342 | |
| | | | Upper limit | 47.8408 | |
| | | 5% trimmed mean | | 34.2083 | |
| | | Median | | 35.5000 | |
| | | Variance | | 266.710 | |
| | | Standard deviation | | 16.33125 | |
| | | Minimum | | 11.50 | |
| | | Maximum | | 56.50 | |
| | | Range | | 45.00 | |
| | | Interquartile range | | 31.63 | |
| | | Asymmetry | | −.217 | .752 |
| | | Kurtosis | | −1.197 | 1.481 |
| | NBT-modified | Mean | | 31.1250 | 6.41757 |
| | | Confidence interval for the mean at 95% | Lower limit | 15.9498 | |
| | | | Upper limit | 46.3002 | |
| | | 5% trimmed mean | | 30.2778 | |
| | | Median | | 23.7500 | |
| | | Variance | | 329.482 | |
| | | Standard deviation | | 18.15164 | |
| | | Minimum | | 11.50 | |
| | | Maximum | | 66.00 | |
| | | Range | | 54.50 | |
| | | Interquartile range | | 25.50 | |
| | | Asymmetry | | 1.077 | .752 |
| | | Kurtosis | | .559 | 1.481 |
| DS | Normal agaroses | Mean | | 14.0000 | 5.09814 |
| | | Confidence interval for the mean at 95% | Lower limit | 1.9448 | |
| | | | Upper limit | 26.0552 | |
| | | 5% trimmed mean | | 13.1389 | |
| | | Median | | 9.0000 | |
| | | Variance | | 207.929 | |
| | | Standard deviation | | 14.41973 | |
| | | Minimum | | 1.00 | |
| | | Maximum | | 42.50 | |
| | | Range | | 41.50 | |
| | | Interquartile range | | 20.38 | |
| | | Asymmetry | | 1.192 | .752 |
| | | Kurtosis | | .944 | 1.481 |
| | NBT-modified | Mean | | 11.3125 | 3.62892 |
| | | Confidence interval for the mean at 95% | Lower limit | 2.7315 | |
| | | | Upper limit | 19.8935 | |

TABLE 3-continued

| Descriptive statistics of the samples | | | |
|---|---|---|---|
| Type | | Statistic | Standard error |
| | 5% trimmed mean | 11.0139 | |
| | Median | 9.7500 | |
| | Variance | 105.353 | |
| | Standard deviation | 10.26415 | |
| | Minimum | .00 | |
| | Maximum | 28.00 | |
| | Range | 28.00 | |
| | Interquartile range | 18.75 | |
| | Asymmetry | .495 | .752 |
| | Kurtosis | −1.141 | 1.481 |

Next, for verifying adjustment of the data to a probability distribution, two nonparametric tests were performed, namely the Kolmogorov-Smirnov test and the Shapiro-Wilk test, data shown in Table 4.

TABLE 4

| Studies of normality of the variables SDF and DS | | | | | | | |
|---|---|---|---|---|---|---|---|
| | | Kolmogorov-Smirnov(a) | | | Shapiro-Wilk | | |
| | type | Statistic | df | Sig. | Statistic | df | Sig. |
| SDF | normal agaroses | .147 | 8 | .200 | .951 | 8 | .721 |
| | modified | .236 | 8 | .200 | .896 | 8 | .263 |
| DS | normal agaroses | .222 | 8 | .200 | .860 | 8 | .121 |
| | modified | .180 | 8 | .200 | .927 | 8 | .491 |

SDF: Sperm DNA fragmentation,
DS: degraded sperm,
df: degrees of freedom,
Sig: significance.

Figure 4:
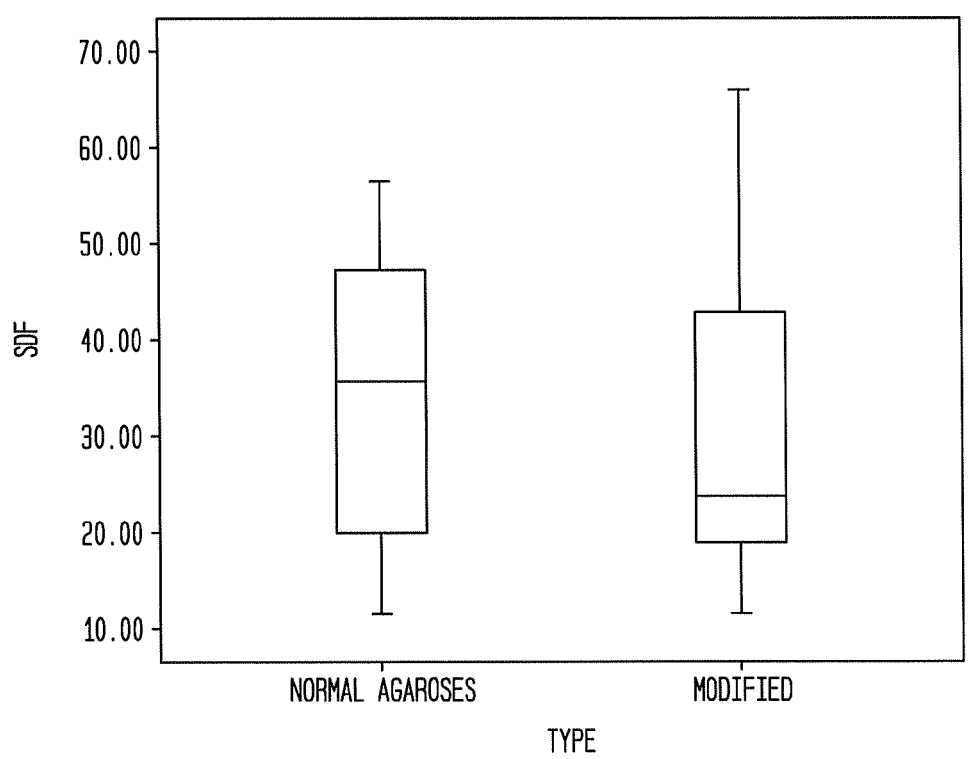
FIG. 4. Box-and-whisker plot showing the data obtained for the variable SDF (percentage of sperm with DNA fragmentation) depending on the type of agarose used: normal (left), modified with NBT (right).
Figure 5:
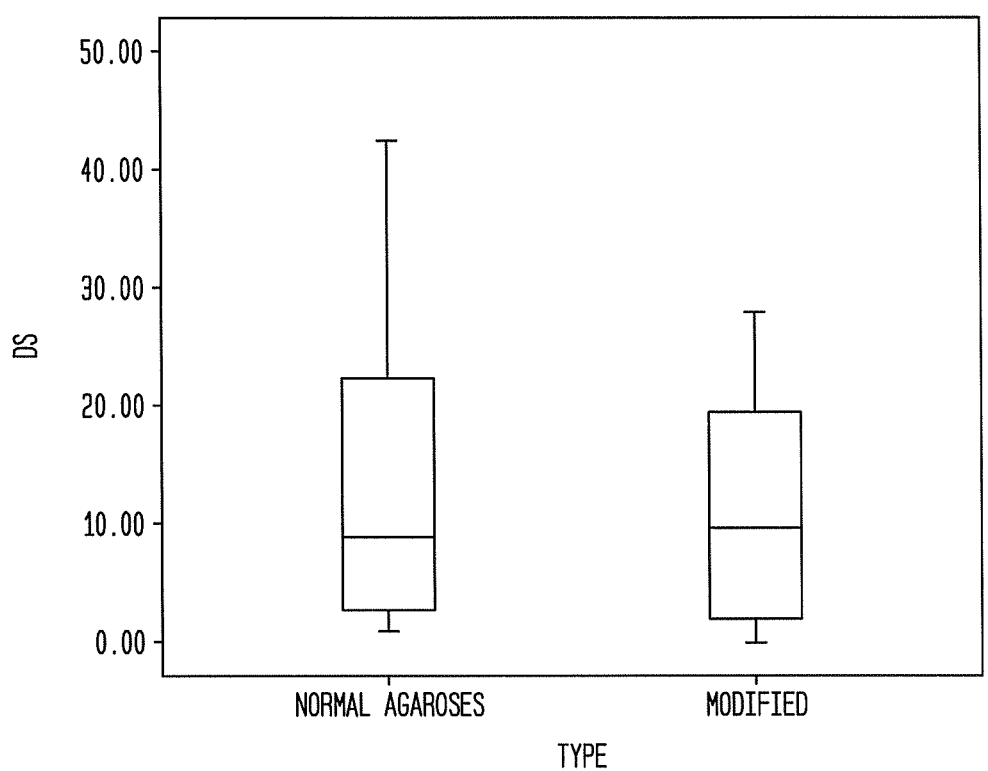
FIG. 5. Box-and-whisker plot showing the data obtained for the variable DS (percentage of degraded sperm) depending on the type of agarose used: normal (left), modified with NBT (right).

One of the steps prior to verification of whether there are differences between the means of several samples is to determine whether the variances in said samples are equal. After performing the Levene Test, it was accepted that both for the variable SDF (Table 5 and FIG. 4), and for the variable DS (Table 6 and FIG. 5) the variances were equal and after them, the means were equal.

TABLE 5

| Results of the test for the variable SDF | | | | | | | | | |
|---|---|---|---|---|---|---|---|---|---|
| | | Levene test for the equality of variances | | T test for the equality of means | | | | | |
| | | | | | | Sig. | Difference | Standard error of the | 95% confidence interval for the difference | |
| | | F | Sig. | t | df | (bilateral) | of means | difference | Upper | Lower |
| DS | Equal variances were assumed | .821 | .380 | .429 | 14 | .674 | 2.68750 | 6.25781 | −10.73416 | 16.10916 |
| | Equal variances were not assumed | | | .429 | 12.644 | .675 | 2.68750 | 6.25781 | −10.87042 | 16.24542 |

TABLE 6

Results of the test for the variable DS

| | Levene test for the equality of variances | | T test for the equality of means | | | | | 95% confidence interval for the difference | |
|---|---|---|---|---|---|---|---|---|---|
| | F | Sig. | t | df | Sig. (bilateral) | Difference of means | Standard error of the difference | Upper | Lower |
| DS Equal variances were assumed | .821 | .380 | .429 | 14 | .674 | 2.68750 | 6.25781 | −10.73416 | 16.10916 |
| Equal variances were not assumed | | | .429 | 12.644 | .675 | 2.68750 | 6.25781 | −10.87042 | 16.24542 |

It was therefore concluded that the agarose NBT used in the method of the present invention is compatible with the agarose of the Halosperm kit for determining sperm DNA and on being treated with two related variables, fragmentation and oxidative stress, optimization of this method could represent a convenient presentation that would allow simultaneous determination of sperm DNA fragmentation and oxidative stress from a small volume of semen sample with a much reduced economic cost.

The invention claimed is:

1. A method for identifying sperm in a cellular population containing reactive oxygen species, comprising sequentially a) through d):
   a) contacting a cellular population of sperm with a thickening agent containing an indicator compound, said cellular population of sperm moving with reduced motility in said thickening agent;
   b) maintaining said mixture obtained in a) in conditions to avoid gelling over a period of time to convert of said indicator compound to a detectable compound in said sperm containing said reactive oxygen species;
   c) placing the mixture obtained in b) on a solid support in conditions suitable to gel said mixture to immobilize said cellular population of sperm; and
   d) identifying said sperm in said cellular population of sperm in which said detectable compound appears, said detectable compound appearing in said sperm indicative of said sperm containing said reactive oxygen species.

2. The method of claim 1, further comprising:
   measuring optical density of said mixture after maintaining said mixture obtained in a) for said sufficient time for conversion of said indicator to said detectable compound; and determining concentration of said detectable compound in said mixture, wherein an increase in concentration of said detectable compound in said mixture relative to a reference sample indicative of the presence of reactive oxygen species in said cellular population of sperm.

3. The method of claim 1, further comprising: incubating a sample of said mixture from b) in conditions suitable for causing breakage of said sperm; and detecting formation of halos around a head of said sperm, wherein presence of said halos greater than a threshold value indicates said cells have intact DNA.

4. The method of claim 1, further comprising staining said sperm from c).

5. The method of claim 1, wherein said thickening agent comprises agarose.

6. The method of claim 5, wherein said agarose has a final concentration of between about 1% to about 2.5%, and wherein b) has a duration of about 45 minutes at about 37° C.

7. The method of claim 1, further comprising placing said mixture obtained in b) with a gelling agent on said solid support in conditions suitable for gelling of said mixture to immobilize said cellular population of sperm.

8. The method of claim 7, wherein said gelling agent is selected from the group consisting of: alginic acid, alginate, agar, carrageenans, locust bean gum, guar gum, gum tragacanth, gum arabic, xanthan gum, karaya gum, tara gum, gellan gum, sorbitol, and sorbitol syrup, mannitol, polvoxyethylene sorbitan monolaurate, polvoxyethylene sorbitan monooleate, polvoxyethylene sorbitan monopalmitate, polyoxvethylene sorbitan monostearate, polyoxyethylene sorbitan tristearate, pectin, ammonium phosphatides, sucrose acetate isobutyrate, glyceride esters of wood rosin cellulose, and combinations or derivatives thereof.

9. The method of claim 1 wherein said indicator compound in the presence of said reactive oxygen species is detectable as a tetrazolium salt.

10. The method of claim 9, wherein said indicator compound comprises a nitroblue tetrazolium.

11. The method of claim 10, wherein d) further comprises identifying said sperm by direct observation by optical microscopy.

12. The method of claim 11, wherein said population of sperm comprise a part of a semen sample.

13. A method for determining the need for antioxidant therapy of a patient, comprising:
   determining the presence of said sperm containing reactive oxygen species in a semen sample from said patient using said method of claim 1;
   determining a percentage of said sperm that have DNA fragmentation using said method of claim 3; and
   comparing the percentage of said sperm containing said reactive oxygen species and the percentage of cells containing fragmented DNA to percentages of said cells in a reference sample, and wherein if the percentages are greater than said reference sample said patient should be treated with an antioxidant therapy.

* * * * *

UNITED STATES PATENT AND TRADEMARK OFFICE
CERTIFICATE OF CORRECTION

PATENT NO. : 9,618,503 B2
APPLICATION NO. : 13/883562
DATED : April 11, 2017
INVENTOR(S) : Jordi Benet Catala It is certified that error appears in the above-identified patent and that said Letters Patent is hereby corrected as shown below:

On the Title Page

Column 2 item [56], Line 16, change "Productioin in Pahgocytic" to --Production in Phagocytic--.

Column 2 item [56], Line 31, change "o" to --of--.

Column 1 page 2, item [56], Line 12, change "Fertiity" to --Fertility--.

Column 1 page 2, item [56], Line 31, change "caricoceles" to --varicoceles--.

In the Specification

Column 6 Line 26, Change "TR-2," to --TR-2.--.

Column 6 Line 27, After "polymers" insert --.--.

Columns 13-14 (Table 2) Line 16, Change "Astrogalus" to --Astragalus--.

Columns 13-14 (Table 2) Line 35, Change "hydroxypropylmethyl cellulose" to --hydroxypropylmethylcellulose--.

Column 13 Line 56, Change "(Lopza)," to --(Lonza),--.

Column 17 Line 32, Change "Therapy." to --Therapy--.

In the Claims

Column 26 Lines 35-36, Claim 8, change "polvoxyethylene" to --polyoxyethylene--.

Signed and Sealed this
Seventeenth Day of October, 2017

Joseph Matal
*Performing the Functions and Duties of the
Under Secretary of Commerce for Intellectual Property and
Director of the United States Patent and Trademark Office*

Column 26 Line 36, Claim 8, change "polvoxyethylene" to --polyoxyethylene--.

Column 26 Line 37, Claim 8, change "polvoxyethylene" to --polyoxyethylene--.